(12) United States Patent
Jan et al.

(10) Patent No.: US 6,238,703 B1
(45) Date of Patent: May 29, 2001

(54) CONTROLLED RELEASE ORAL DOSAGE FORM OF KETOPROFEN

(75) Inventors: Steve Jan, Coral Springs; Xiu Xiu Cheng; Chih-Ming Chen, both of Davie, all of FL (US)

(73) Assignee: Andrx Pharmaceuticals, Inc., Davie, FL (US)

( * ) Notice: Subject to any disclaimer, the term of this patent is extended or adjusted under 35 U.S.C. 154(b) by 0 days.

(21) Appl. No.: 09/637,404

(22) Filed: Aug. 11, 2000

Related U.S. Application Data

(63) Continuation of application No. 09/106,609, filed on Jun. 29, 1998.

(51) Int. Cl.[7] ............................. A61K 9/14; A61K 9/16
(52) U.S. Cl. ..................... 424/495; 424/489; 424/490; 424/493; 424/494; 424/496; 514/570
(58) Field of Search ................ 514/570; 424/451, 424/457, 458, 459, 461, 464, 468, 469, 489, 490, 493, 494, 495, 496

(56) References Cited

U.S. PATENT DOCUMENTS

| | | |
|---|---|---|
| 4,166,800 | 9/1979 | Fong . |
| 4,256,785 | 3/1981 | Dannelly . |
| 4,344,929 | 8/1982 | Bonsen et al. . |
| 4,393,076 | 7/1983 | Noda et al. . |
| 4,421,747 | 12/1983 | Ghyczy et al. . |
| 4,486,436 | 12/1984 | Sunshine et al. . |
| 4,522,826 | 6/1985 | Sunshine et al. . |
| 4,568,559 | 2/1986 | Nuwayser et al. . |
| 4,600,645 | 7/1986 | Ghebre-Sellassie et al. . |
| 4,623,588 | 11/1986 | Nuwayser et al. . |
| 4,722,938 | 2/1988 | Sunshine et al. . |
| 4,753,801 | 6/1988 | Oren et al. . |
| 4,761,407 | 8/1988 | Campan et al. . |
| 4,783,337 | 11/1988 | Wong et al. . |
| 4,801,460 | 1/1989 | Goertz et al. . |
| 4,844,907 | 7/1989 | Elger et al. . |
| 4,867,985 | 9/1989 | Heafield et al. . |
| 4,868,214 | 9/1989 | Sunshine et al. . |
| 4,917,899 | 4/1990 | Geoghegan et al. . |
| 4,980,170 | 12/1990 | Schneider et al. . |
| 5,080,907 | 1/1992 | Iijima et al. . |
| 5,087,455 | 2/1992 | Niwa et al. . |
| 5,133,974 | 7/1992 | Paradissis et al. . |
| 5,149,542 | * 9/1992 | Valducci . |
| 5,171,580 | 12/1992 | Iamartino et al. . |
| 5,188,841 | 2/1993 | Simpkin et al. . |
| 5,202,129 | 4/1993 | Samejima et al. . |
| 5,288,503 | 2/1994 | Wood et al. . |
| 5,331,000 | 7/1994 | Young et al. . |

(List continued on next page.)

FOREIGN PATENT DOCUMENTS 0 061 217 * 9/1982 (EP) .

OTHER PUBLICATIONS

Physician's Desk Reference, 50th Ed. p. 2767–2771.

Primary Examiner—Thurman K. Page
Assistant Examiner—Brian K. Seidleck
(74) Attorney, Agent, or Firm—Hedman & Costigan, P.C.

(57) ABSTRACT

A controlled release analgesic dosage form comprising: a core comprising an analgesic and binding agent; and a coating comprising an enteric polymer, a water insoluble second polymer and a lubricant.

12 Claims, 4 Drawing Sheets

U.S. PATENT DOCUMENTS

| | | |
|---|---|---|
| 5,348,745 | 9/1994 | Daher . |
| 5,348,747 | 9/1994 | Bianco . |
| 5,354,560 | 10/1994 | Lovrecich . |
| 5,424,075 | 6/1995 | Daher et al. . |
| 5,431,916 | 7/1995 | White . |
| 5,445,829 * | 8/1995 | Paradissis et al. . |
| 5,449,521 | 9/1995 | Lovrecich . |
| 5,464,633 | 11/1995 | Conte et al. . |
| 5,474,989 | 12/1995 | Hashimoto et al. . |
| 5,489,439 | 2/1996 | Bola . |
| 5,505,983 * | 4/1996 | Kamada . |
| 5,516,531 | 5/1996 | Makino et al. . |
| 5,552,160 | 9/1996 | Liversidge et al. . |
| 5,591,456 | 1/1997 | Franson et al. . |
| 5,624,682 | 4/1997 | Dondi et al. . |
| 5,624,962 | 4/1997 | Takeuchi et al. . |
| 5,654,004 | 8/1997 | Okayama et al. . |
| 5,656,286 | 8/1997 | Miranda et al. . |
| 5,667,807 | 9/1997 | Hürner et al. . |
| 5,955,104 * | 9/1999 | Momberger et al. . |
| 5,968,551 * | 10/1999 | Oshlack et al. . |

* cited by examiner

CONTROLLED RELEASE ORAL DOSAGE FORM OF KETOPROFEN

This Appln is a continuation of U.S. Ser. No. 09/106,609 filed Jun. 29, 1998.

BACKGROUND OF THE INVENTION

The present invention relates to oral controlled release dosage formulations containing an analgesic. More specifically, the present invention relates to an oral dosage formulation in the form of a tablet or a capsule containing pellets comprising a nonsteroidal anti-inflammatory drug (NSAID), preferably a propionic acid derivative such as ibuprofen, naproxen, flubiprofen, indoprofen, ketoprofen or there pharmaceutically acceptable derivatives. Most preferably the NSAID is ketoprofen.

Numerous techniques are in the prior art for preparing sustained or controlled release pharmaceutical formulations. One common technique involves surrounding an osmotically active drug core with a semipermeable membrane. The drug is released from the core over time by allowing a fluid such as gastric or intestinal fluid to permeate the coating membrane and dissolve the drug so the dissolved drug can permeate the membrane. In some cases a hydrogel is employed to push the active ingredient through the passageway in the membrane. Some representative examples of these osmotic tablet systems can be found in U.S. Pat. Nos. 3,845,770, 3,916,899, 3,952,741, 4,034,758, 4,077,407 and 4,783,337.

Another common technique for preparing controlled release pharmaceutical formulations is to encapsulate a plurality of beads, pellets or tablets that are coated with varying levels of a diffusion barrier and/or different types of the diffusion barriers. Examples of these beaded formulations can be found in U.S. Pat. Nos. 5,376,384, 5,529,790, 5,470,584, 5,002,776, 5,445,829 and 5,578,321. The product ORUVAIL® which is commercially available from Wyeth-Ayerst Laboratories, is another example of a controlled release pharmaceutical formulation that employs the bead technology. The ORUVAIL® product is available in 100 mg, 150 mg and 200 mg capsules and contains hundreds of coated pellets that consist of ketoprofen, ethylcellulose, gelatin, shellac, silicon dioxide, sodium lauryl sulfate, starch, sucrose, talc, titanium dioxide, dyes and other proprietary ingredients.

It is an object of the present invention to provide a controlled or sustained release dosage formulation for an analgesic that is easy to manufacture and can be used to prepare a range of dosing levels.

It is a further object of the present invention to provide a controlled or sustained release dosage formulation for an analgesic that can be prepared with only one coating layer.

It is an additional object of the present invention to provide a controlled or sustained release dosage formulation for an analgesic that can provide continuous and non-pulsating therapeutic levels of the analgesic to an animal or human in need of such treatment over a twelve hour to twenty-four hour period.

SUMMARY OF THE INVENTION

The foregoing objectives are met by a controlled release dosage form comprising:
(a) a core comprising:
  (i) an analgesic;
  (ii) an inert pellet as a starting material; and
  (ii) a binding agent; and
(b) a coating comprising:
  (i) an enteric polymer;
  (ii) a water insoluble second polymer; and
  (iii) a lubricant or dusting agent.

The core comprises about 80 to about 99 weight percent of the total dosage form and preferably about 85 to 98 weight percent of the dosage form.

The ratio of the enteric polymer to the second polymer in the coating should be about 1:1 to 2:1, preferably 1.25:1 to 1.75:1 and most preferably about 1.5:1. These preferred ratios are based upon the weight of the enteric polymer to the weight of the second polymer.

In a preferred embodiment the binder and the second polymer are the same material but with different viscosities such that the binder has a higher viscosity than the second polymer in the coating.

The dosage form of the present invention can provide therapeutic levels of the analgesic for twelve to twenty-four hour time periods and does not obtain peak plasma levels for at least 4 hours, ideally 8 to 12 hours, after administration.

DETAILED DESCRIPTION OF THE INVENTION

Figure 1:
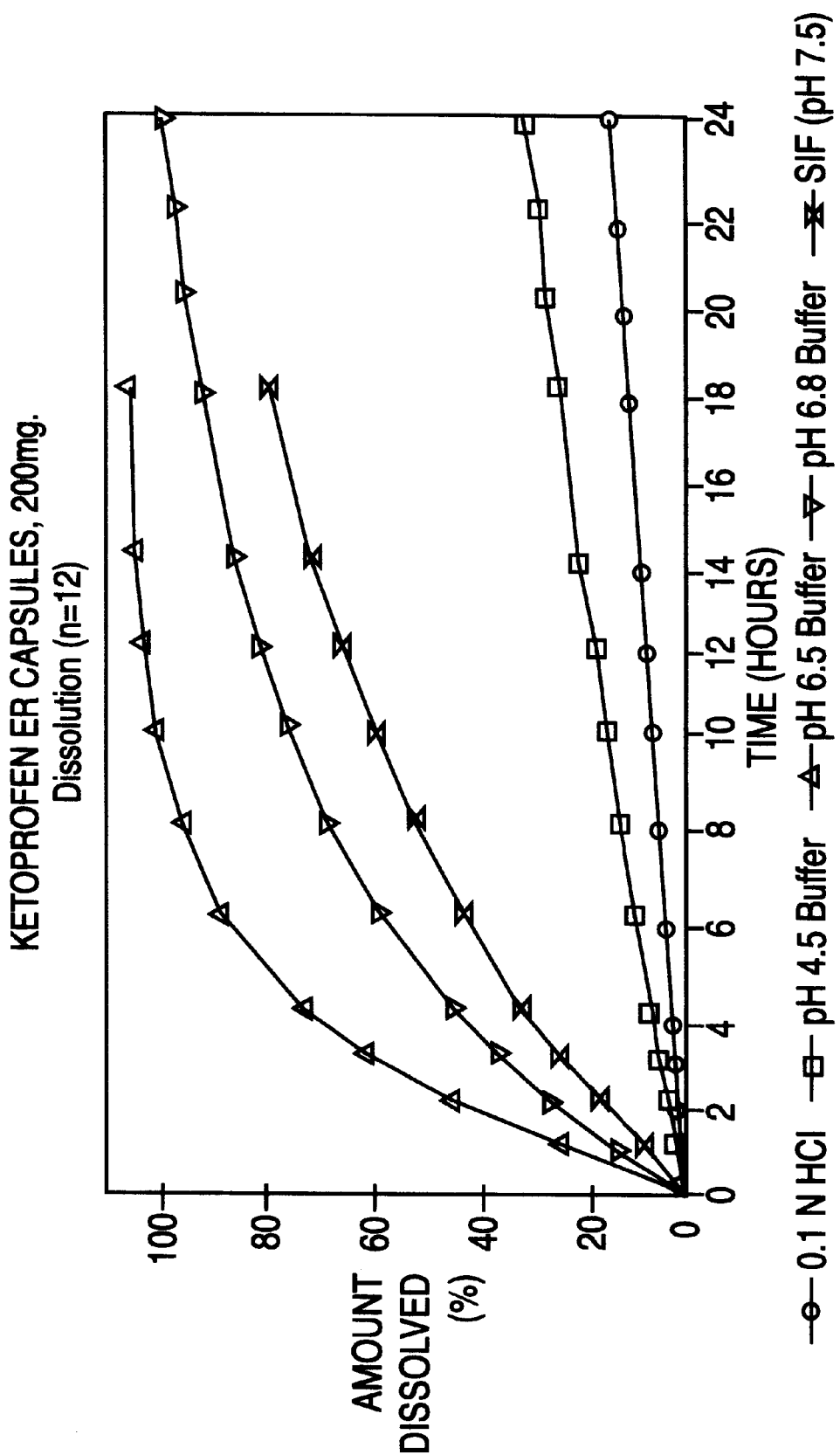
FIG. 1 is a graph depicting the dissolution profile in simulated intestinal fluid (pH 7.5 phosphate buffer), pH 6.5, pH 6.8, pH 4.5 and 0.1N HCl of the formulation described in Example 1 as tested according to the procedure described in United States Pharmacopeia XXIII, Apparatus 2 @ 75 rpm.
Figure 2:
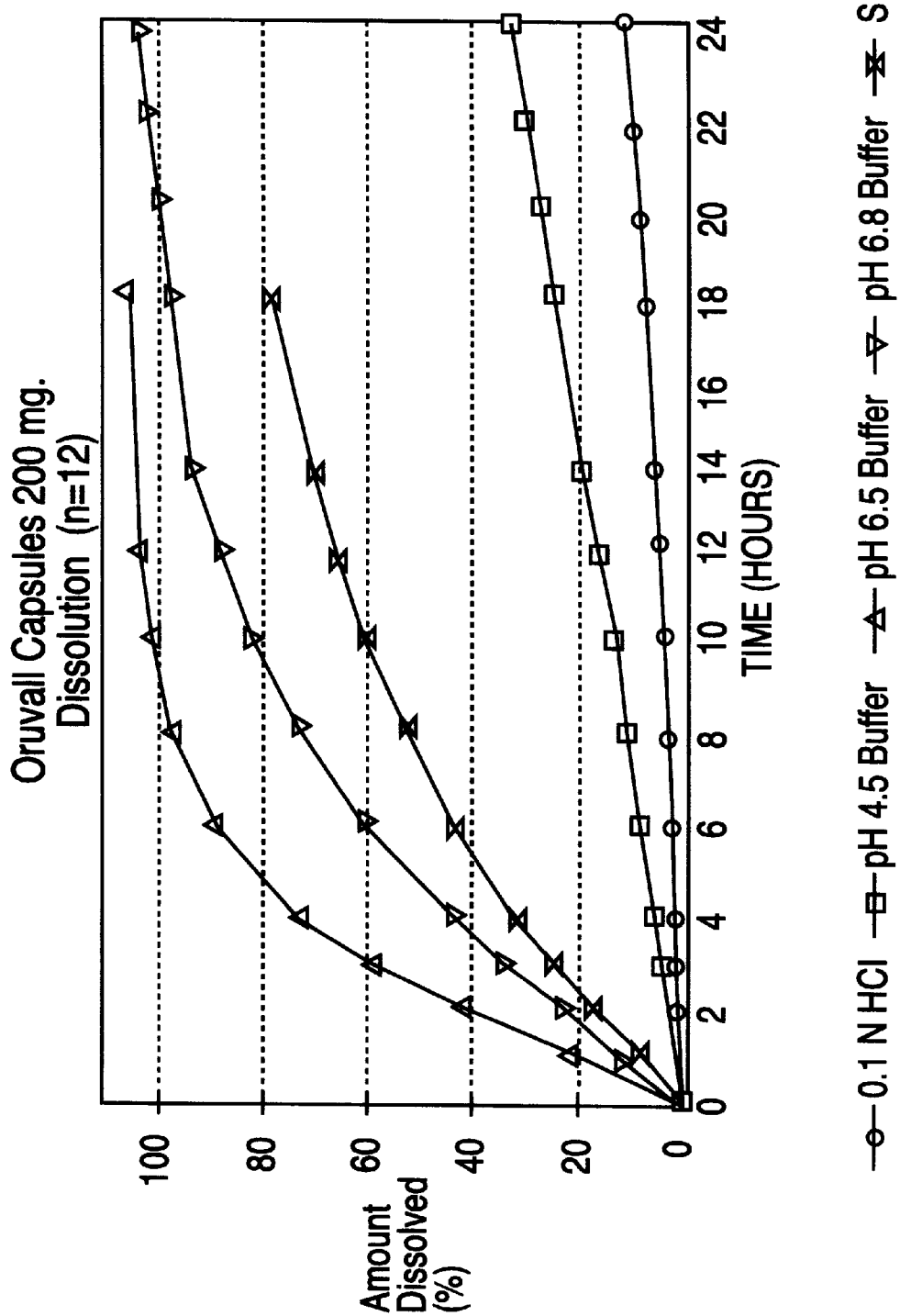
FIG. 2 is a graph depicting the dissolution profile in simulated intestinal fluid (pH 7.5 phosphate buffer), pH 6.5, pH 6.8, pH 4.5 and 0.1N HCl of the commercially available ketoprofen product ORUVAIL® as tested according to the procedure described in United States Pharmacopeia XXIII, Apparatus 2 @ 75 rpm.

The term analgesic as used in this specification refers to drugs that are useful in relieving or controlling pain without disturbing consciousness or altering other sensory modalities. The analgesic may be an opiate such a morphine or codeine or a non-opiate such as acetaminophen, aspirin, ibuprofen, naproxen and ketoprofen. Other analgesics are described in Remington's Pharmaceutical Sciences, 1995 Edition and are incorporated herein by reference.

The preferred analgesic for use in the present invention is a propionic acid derivative such as ibuprofen, naproxen, flubiprofen, indoprofen, ketoprofen or a pharmaceutically acceptable derivative thereof. The most preferred analgesic is ketoprofen such as described in U.S. Pat. Nos. 3,641,127, 5,331,000 and 4,868,214. The ketoprofen should be micronized and preferably have a particle size of less than 20 microns.

The inert pellet starting material can be any type of commonly known pellet starting material such as a starch or sugar sphere having a diameter ranging from about 15–50 mesh and more preferably about 30–35 mesh.

The binding agent employed in the core can be any type of binding agent commonly known in the art such as polyvinyl pyrrolidone, hydroxyethylcellulose, hydroxypropyl cellulose, hydroxypropyl methycellulose, polymethacrylate or ethylcellulose. In the preferred embodiment of the present invention, the binding agent is a water insoluble polymer such as ethylcellulose with a viscosity of about 8–12 cps, preferably 9–11 cps and most preferably about 10 cps.

The core of the present invention will comprise the following ingredients:

| INGREDIENT | PREFERRED | MOST PREFERRED |
| --- | --- | --- |
| ketoprofen | 50–90% | 70–80% |
| binding agent | 0.5–7.5% | 2–5% |
| starting pellet | 10–35% | 15–30%. |

All the percentages in the above table are based on the total weight of the core.

The core of the present invention which comprises the analgesic is prepared by forming a suspension of the binder and drug and then layering the suspension onto the starting pellet using any of the layering techniques known in the industry such as fluidized bed coating, rotor granulation or pan coating.

The coating layer that is applied to the core to control the release of the drug from the dosage form comprises an enteric polymer, a second polymer that is a water insoluble polymer and a lubricating or dusting agent.

Suitable enteric polymers are shellac, cellulose acetate phthalate, hydroxypropyl methycellulose phthalate, polyvinyl acetate phthalate, methacrylic acid polymers such as Eudragit S, Eudragit S100, Eudragit L30D, or Eudragit L100 or a mixture of the foregoing. Shellac is the preferred enteric polymer.

Suitable water insoluble polymers for use as the second polymer are polymers that are permeable to stomach and/or intestinal fluid and comprise polymers such as ethylcellulose, cellulose acetate, cellulose propionate, cellulose acetate propionate, cellulose acetate butyrate, cellulose acetate phthalate, cellulose triacetate, polymethyl methacrylate, polyethyl methacrylate, polybutyl methacrylate, polyisobutyl methacrylate, polyhexyl methacrylate, poly isodecyl methacrylate, polylauryl methacrylate, polyphenyl methacrylate, polymethyl acrylate, polyisopropyl acrylate, polyisobutyl acrylate, polyoctadecyl acrylate, polyethylene, polypropylene, polyethylene oxide, polyethylene terephthalate, polyvinyl isobutyl ether, polyvinyl acetate, polyvinyl chloride, polyurethane or a mixture thereof. In the preferred embodiment of the present invention, the second polymer is ethylcellulose with a viscosity below 9 cps, preferably about 5.6 to 8.4 cps and most preferably about 7 cps.

Suitable lubricants or dusting agents that can be used in the present invention are talc, magnesium stearate, silicon dioxide, kaolin or a mixture of the foregoing. The lubricant or dusting agent prevents the pellets from sticking to one another during processing. The lubricant may be dusted onto the active pellets during the coating process or it may be incorporated into a coating suspension and applied to the core with the coating suspension.

The coating layer can be applied to the core by any means commonly known in the industry, however, if the lubricant is to be dusted onto the cores during the coating process it is preferred to use a rotary granulator for the coating process. If the lubricant is applied to the cores by suspending it in the coating solution, it is preferred to use a fluidized bed coater for the coating process.

In a preferred embodiment the coating of the present invention will have the following composition:

| COATING: | Preferred | Most Preferred |
| --- | --- | --- |
| enteric polymer | 20–70% | 25–45% |
| second polymer | 15–40% | 20–35% |
| lubricant | 25–75% | 30–60%. |

The percentages listed in the above table are based on the total weight of the coating.

Generally, the coating layer will comprise from about 1% to about 20% and preferably about 1.5% to about 15% based on the total weight of the core and coating.

The dosage form of the present invention may also comprise an effective amount of the analgesic for immediate release. The effective amount of analgesic for immediate release may be applied onto the coating layer than covered with a seal coating or incorporated onto the coating layer during processing.

The dosage form may also comprises a mixture of controlled release pellets as described above and immediate release pellets. The immediate release pellets are identical to the above-described core but do not employ a controlled release coating layer. If the immediate release pellets do employ a coating layer, the coating layer must comprise a rapidly disintegrating material or an immediately soluble material such as OPADRY. The controlled release pellet and the immediate release pellet are placed in a hard gelatin capsule for administration to an animal or human in need of analgesic treatment.

The controlled release dosage forms prepared according to the present invention should exhibit the following dissolution profile when tested in a USP type 2 apparatus at 75 rpms in 900 ml of simulated intestinal fluid (pH 7.5 phosphate buffer) and at 37° C.:

| Time (hours) | Preferred | Most Preferred |
| --- | --- | --- |
| 2 | 20–60% | 30–60% |
| 4 | 30–90% | 45–85% |
| 8 | NTL 50% | NTL 60% |
| 12 | NTL 60% | NTL 70% |
| 18 | NTL 70% | NTL 80% |

NTL = NOT LESS THAN

The controlled release dosage forms prepared according to the present invention should exhibit the following dissolution profile when tested in a USP type 2 apparatus at 75 rpms in 900 ml of pH 6.5 phosphate buffer and at 37° C.:

| Time (hours) | Preferred | Most Preferred |
| --- | --- | --- |
| 2 | 0–50% | 5–40% |
| 4 | 10–60% | 15–50% |
| 8 | 20–80% | 35–70% |

-continued

| Time (hours) | Preferred | Most Preferred |
|---|---|---|
| 12 | 35–85% | 45–80% |
| 18 | NTL 60% | NTL 70% |
| 24 | NTL 70% | NTL 80% |

NTL = NOT LESS THAN

The controlled release dosage forms prepared according to the present invention should exhibit the following dissolution profile when tested in a USP type 2 apparatus at 75 rpms in 900 ml of pH 6.8 phosphate buffer and at 37° C.:

| Time (hours) | Preferred | Most Preferred |
|---|---|---|
| 2 | 0–50% | 10–40% |
| 4 | 20–65% | 30–60% |
| 8 | 40–85% | 50–80% |
| 12 | NTL 60% | NTL 70% |
| 18 | NTL 70% | NTL 80% |

NTL = NOT LESS THAN

DESCRIPTION OF THE PREFERRED EMBODIMENTS

The following example illustrates the present invention and is not intended to limit the scope of the present invention.

EXAMPLE 1

A controlled release oral analgesic dosage form in accordance with the present invention is prepared by forming an active or immediate release core having the following composition:

| I ACTIVE CORE | |
|---|---|
| ketoprofen[1], BP or USP | 75.0% |
| sugar sphere, NF[2] | 22.5% |
| ethylcellulose (ETHOCEL 10 cps) | 2.5% |

[1] racemic mixture with an average particle size of less than 20 microns.
[2] 30/35 mesh.

The active core is prepared by adding 0.408 kg of the ethylcellulose into 12.648 kg of isopropyl alcohol while mixing with a homogenizer. Once the ethylcellulose is dissolved, 12.240 kg of ketoprofen is added to the above solution while mixing until a uniform suspension is obtained. The ethylcellulose/ketoprofen suspension is then applied to 11.325 kg of the sugar spheres in a fluidized bed coater under the following conditions: product temperature is 30–35° C.; atomization pressure is 2–3 bar; and the pump rate is 5 to 200 ml/min.

After all the ethylcellulose/ketoprofen suspension is consumed, the in-process ketoprofen active pellets will contain approximately 51% ketoprofen based upon the total weight of the in-process active pellet. The in process ketoprofen active pellets are then coated with a second batch of ethylcellulose/ketoprofen suspension that is prepared as described above and coated onto the in process ketoprofen active pellets in a fluidized bed coater as described above until the ketoprofen active pellets comprise approximately 75% ketoprofen based upon the total weight of the ketoprofen active pellets.

Once the target amount of ketoprofen is applied to the active cores, the active cores are dried in the fluidized bed coater for approximately 35 minutes±10 minutes or until the LOD (loss on drying) is less than 1%. Once the drying stage is completed, the dried ketoprofen active pellets are placed in a clean, properly labeled double polyethylene bag lined container.

The active cores are coated with a controlled release coating wherein the controlled release coating has the following composition:

| II Sustained Release Coating | |
|---|---|
| shellac | 36.89% |
| ethylcellulose (ETHOCEL 7 cps) | 24.76% |
| talc | 38.35% |

The controlled release coating is prepared by adding 0.069 kg of the ethylcellulose and 0.103 kg of shellac to 1.548 kg of denatured ethanol while mixing with a stirrer until both the ethylcellulose and shellac are dissolved. The controlled release coating solution is then applied to the active cores, while dusting with talc at a powder feed rate of 3.5 to 5.0 g/min, using a Glatt rotary granulator under the following conditions: rotor speed of 175±5 rpm; inlet temperature of 23° C.±5° C.; atomization pressure of 2–3 bar; and a pump rate of 80–120 g/min. The coating is continued until a theoretical coating level of approximately 2% is obtained.

After the theoretical coating level is obtained the coated cores are dried in an oven at 65° C.±5° C. for 16 to 20 hours.

The controlled release coated pellets have the following composition:

| III CONTROLLED RELEASE COATED PELLETS | |
|---|---|
| sugar sphere | 21.92% |
| ketoprofen | 73.57% |
| ethylcellulose (ETHOCEL 10 cps) | 2.45% |
| shellac | 0.76% |
| ethylcellulose (ETHOCEL 7 cps) | 0.51% |
| talc | 0.79% |

The resulting controlled release coated pellets were encapsulated into hard gelatin capsules and were tested in simulated intestinal fluid (pH 7.5 phosphate buffer), pH 6.5, pH 6.8, pH 4.5 and 0.1N HCl according to the procedure described in United States Pharmacopeia XXIII, using Apparatus 2 @ 75 rpm and found to have the following release profile:

| TIME (hours) | SIF % Released | pH 6.5 % Released | pH 6.8 % Released | pH 4.5 % Released | 0.1 N HCl % Released |
|---|---|---|---|---|---|
| 2 | 45 | 17 | 25 | 4 | 2 |
| 4 | 73 | 32 | 44 | 7 | 3 |
| 8 | 96 | 53 | 68 | 13 | 6 |
| 12 | 103 | 66 | 81 | 18 | 8 |
| 18 | 105 | 78 | 91 | 24 | 11 |
| 24 | | | | 30 | 14 |

The release profile in pH 7.5, pH 6.5, pH 6.8, pH 4.5 and 0.1N HCl of the controlled release product prepared in this Example is shown in FIG. 1.

Figure 3:
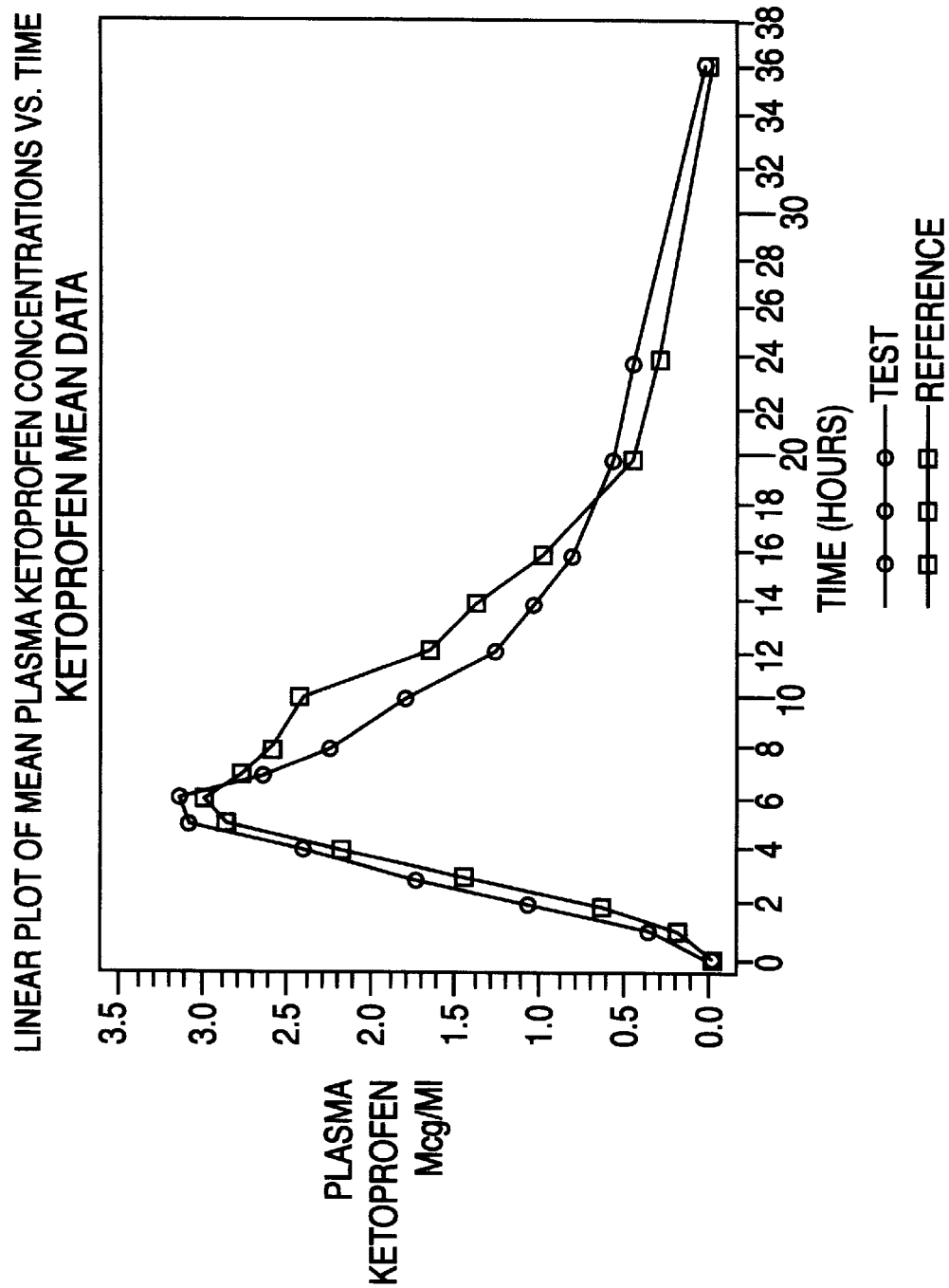
FIG. 3 is a graph depicting the linear plot of the mean plasma ketoprofen concentration verses time of the formulation described in Example 1 and the linear plot of the mean plasma ketoprofen concentration verses time of the commercially available ketoprofen product ORUVAIL®.

FIG. 3 depicts the in vivo ketoprofen plasma profile of the controlled release product prepared in this Example. Also shown in FIG. 3 is the in vivo ketoprofen plasma profile of ORUVAIL®, a commercially available pharmaceutical product containing the drug ketoprofen.

Table 1 is a summary of the bioavailability comparison data under fasting conditions, test/reference ratio, shown in FIG. 3 wherein the ORUVAIL® product is the reference product in a two way crossover biostudy with n=27.

TABLE 1

|  | Test Mean | Ref Mean | G-Mean Ratio |
|---|---|---|---|
| Cmax | 3.713 | 3.529 | 1.05 |
| $AUC_{inf}$ | 36.625 | 36.137 | 1.01 |

Figure 4:
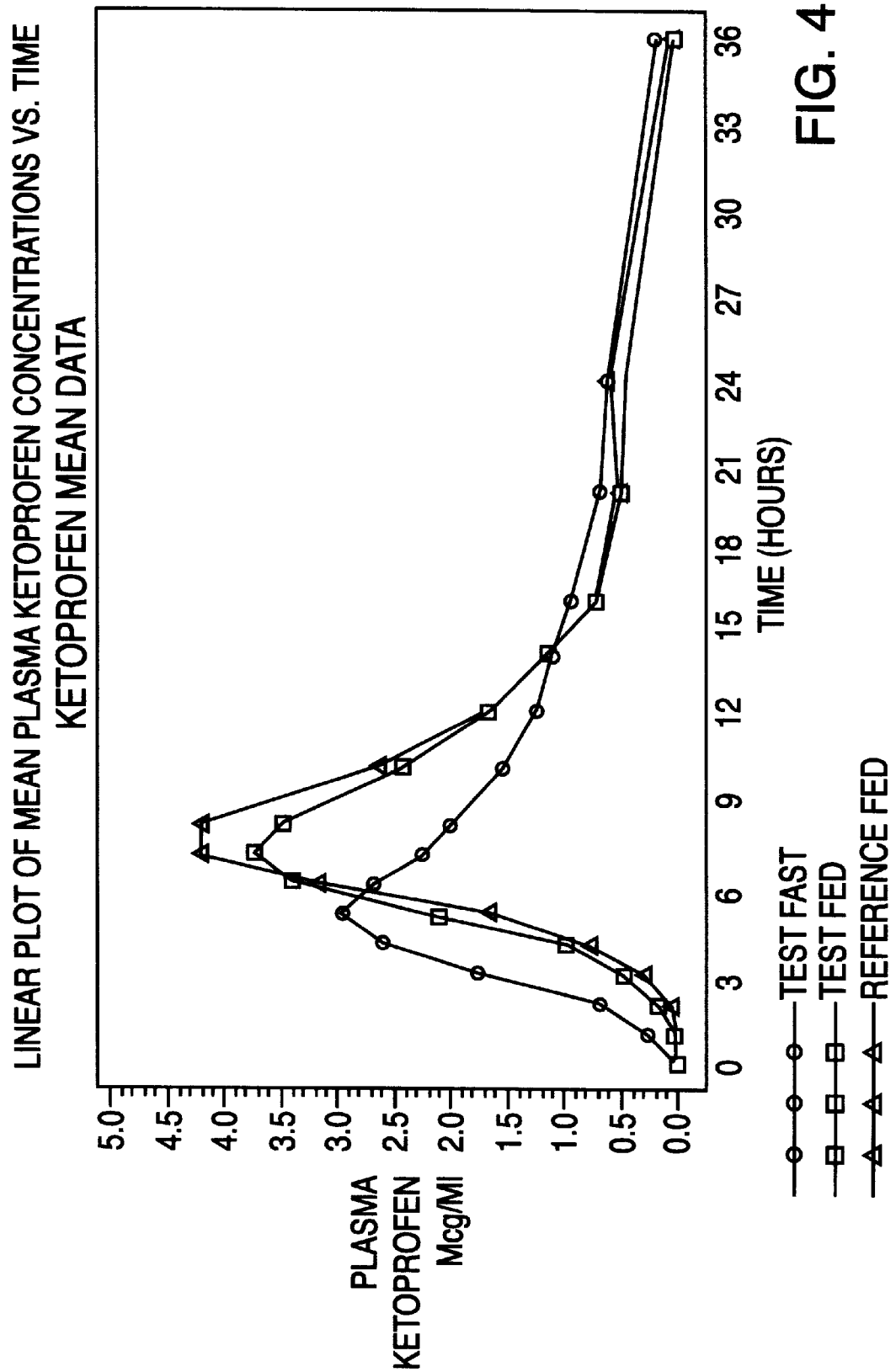
FIG. 4 is a graph depicting the linear plot of the mean plasma ketoprofen concentration verses time of the formulation described in Example 1 under fed and fasting conditions and the linear plot of the mean plasma ketoprofen concentration verses time of the commercially available ketoprofen product ORUVAIL® under fed conditions.

FIG. 4 depicts the in vivo ketoprofen plasma profile of the controlled release product prepared in this Example under fed and fasting conditions. FIG. 4 also shows the in vivo ketoprofen plasma profile of the ORUVAIL® product under fed conditions.

Table 2 is a summary of the bioavailability comparison data under non-fasting conditions, test/reference ratio, shown in FIG. 4 wherein the ORUVAIL® product is the reference product in a three way crossover biostudy with n=24.

TABLE 2

|  | Test Mean | Ref Mean | G-Mean Ratio | A-Mean Ratio |
|---|---|---|---|---|
| Cmax | 4.103 | 4.932 | 0.87 | 0.83 |
| AUC | 36.336 | 37.801 | 0.97 | 0.96 |

EXAMPLE 2

A controlled release oral analgesic dosage form in accordance with the present invention is prepared by forming an active or immediate release core and having the following composition:

| I ACTIVE CORE | |
|---|---|
| ketoprofen[1], BP/USP | 75.0% |
| sugar sphere, NF[2] | 22.5% |
| ethylcellulose (ETHOCEL 10 cps) | 2.5% |

[1]racemic mixture with an average particle size of less than 20 microns.
[2]30/35 mesh.

The active core is prepared by adding 0.6 kg of the ethylcellulose into 18.60 kg of isopropyl alcohol while mixing with a homogenizer. Once the ethylcellulose is dissolved, 18.00 kg of ketoprofen is added to the ethylcellulose solution while mixing until a uniform suspension is obtained. The ethylcellulose/ketoprofen suspension is then applied to 5.4 kg of the sugar spheres in a fluidized bed coater under the same conditions described in Example 1 and dried according to the procedure described in Example 1.

The active cores prepared according to this one step process are coated with a controlled release coating as described in Example 1 to produce a controlled release dosage form in accordance with the present invention that exhibits similar dissolution and bioavailability properties as the controlled release dosage form prepared in Example 1.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A controlled release pharmaceutical dosage form consisting essentially of:
   (a) a core consisting essentially of:
      (i) 50–90% of ketoprofen;
      (ii) 10–35% of an inert pellet starting material; and
      (ii) 0.5–7.5% of ethylcellulose; and
   (b) a coating consisting essentially of:
      (i) 20–70% of shellac;
      (ii) 15–40% of ethylcellulose; and
      (iii) 25–75% of a lubricant,
wherein the viscosity of the core ethylcellulose is 8–12 cps, the viscosity for the coating ethylcellulose is below 9 cps with the proviso that the viscosity of the ethylcellulose in the core is always greater than the viscosity of the ethycellulose in the coating and that exhibits the following dissolution profile when tested in a USP type 2 apparatus at 75 rpm in 900 ml of simulated intestinal fluid, pH 7.5 phosphate buffer and at 37° C.:
   after 2 hours 20–60% of the ketoprofen is released;
   after 4 hours 30–90% of the ketoprofen is released;
   not less than 50% of the ketoprofen is released after 8 hours;
   not less than 60% of the ketoprofen is released after 12 hours; and not less than 70% of the ketoprofen is released after 18 hours.

2. The controlled release pharmaceutical dosage form as defined in claim 1 that exhibits the following dissolution profile when tested in a USP type 2 apparatus at 75 rpm in 900 ml of simulated intestinal fluid, pH 7.5 phosphate buffer and at 37° C.: after 2 hours 30–60% of the ketoprofen is released;
   after 4 hours 45–85% of the ketoprofen is released;
   not less than 60% of the ketoprofen is released after 8 hours;
   not less than 70% of the ketoprofen is released after 12 hours; and not less than 80% of the ketoprofen is released after 18 hours.

3. A controlled release pharmaceutical dosage form consisting essentially of:
   (a) a core consisting essentially of:
      (i) 50–90% of ketoprofen;
      (ii) 10–35% of an inert pellet starting material; and
      (ii) 0.5–7.5% of ethylcellulose; and
   (b) a coating consisting essentially of:
      (i) 20–70% of shellac;
      (ii) 15–40% of ethylcellulose; and
      (iii) 25–75% of a lubricant,
wherein the viscosity of the core ethylcellulose is 8–12 cps, the viscosity for the coating ethylcellulose is below 9 cps with the proviso that the viscosity of the ethylcellulose in the core is always greater than the viscosity of the ethylcellulose in the coating and that exhibits the following dissolution profile when tested in a USP type 2 apparatus at 75 rpm in 900 ml of pH 6.8 phosphate buffer and at 37° C.:
   after 2 hours 0–50% of the ketoprofen is released;
   after 4 hours 20–65% of the ketoprofen is released;
   after 8 hours 40–85% of the ketoprofen is released;
   not less than 60% of the ketoprofen is released after 12 hours; and not less than 70% of the ketoprofen is released after 18 hours.

4. The controlled release pharmaceutical dosage form as defined in claim 3 that exhibits the following dissolution profile when tested in a USP type 2 apparatus at 75 rpm in 900 ml of pH 6.8 phosphate buffer and at 37° C.:

after 2 hours 10–40% of the ketoprofen is released;

after 4 hours 30–60% of the ketoprofen is released;

after 8 hours 50–80% of the ketoprofen is released;

not less than 70% of the ketoprofen is released after 12 hours; and not less than 80% of the ketoprofen is released after 18 hours.

5. The controlled release pharmaceutical dosage form as defined in claim 1 wherein the ratio of the shellac to the ethylcellulose in the coating is about 1:1 to 2:1.

6. The controlled release pharmaceutical dosage form as defined in claim 5 wherein the ratio of the shellac to the ethylcellulose in the coating is about 1.25:1 to 1.75:1.

7. The controlled release pharmaceutical dosage form as defined in claim 6 wherein the ratio of the shellac to the ethylcellulose in the coating is about 1.5:1.

8. The controlled release pharmaceutical dosage form as defined in claim 1 wherein the lubricant is selected from the group consisting of talc, magnesium stearate, silicon dioxide, kaolin and mixtures thereof.

9. The controlled release pharmaceutical dosage form as defined in claim 3 wherein the ratio of the shellac to the ethylcellulose in the coating is about 1:1 to 2:1.

10. The controlled release pharmaceutical dosage form as defined in claim 9 wherein the ratio of the shellac to the ethylcellulose in the coating is about 1.25:1 to 1.75:1.

11. The controlled release pharmaceutical dosage form as defined in claim 9 wherein the ratio of the shellac to the ethylcellulose in the coating is about 1.5:1.

12. The controlled release pharmaceutical dosage form as defined in claim 3 wherein the lubricant is selected from the group consisting of talc, magnesium stearate, silicon dioxide, kaolin and mixtures thereof.

* * * * *